United States Patent [19]

Neyra et al.

[11] Patent Number: 5,589,381
[45] Date of Patent: Dec. 31, 1996

[54] BACILLUS LICHENIFORMIS PRODUCING ANTIFUNGAL AGENTS AND USES THEREOF FOR CONTROL OF PHYTOPATHOGENIC FUNGI

[75] Inventors: Carlos A. Neyra, Kendall Park; Lakshmi Sadasivan, Piscataway, both of N.J.

[73] Assignee: Rutgers, The State University of New Jersey, Piscataway, N.J.

[21] Appl. No.: 268,922

[22] Filed: Jun. 30, 1994

[51] Int. Cl.$^6$ .............................. C12N 1/20; A01N 63/00
[52] U.S. Cl. .................... 435/252.5; 435/836; 424/93.46
[58] Field of Search ...................... 424/93.46; 435/252.5, 435/836

[56] References Cited

U.S. PATENT DOCUMENTS

| | | | |
|---|---|---|---|
| 4,647,537 | 3/1987 | Shigemitsu | 435/178 |
| 5,089,606 | 2/1992 | Cole et al. | 536/54 |

OTHER PUBLICATIONS

Loeffler te al. (1986), J. Phytopathology 115: 204–213.
Vanittanakom et al. (1986), J. Antibiotics 39: 888–901.
Wakayama et al. (1984), Antimicrobial Agents and Chemotherapy 26: 939–940.
Ferreira et al. (1991), J. Phytopathology 81: 283–287.
Claus & Berkeley (1986) "Genus *Bacillus* Cohn 1872 174$^{AL}$", pp. 1104–1139 in *Bergey's Manual of Systematic Bacteriology*, vol. II (Sneath, Mair, Sharpe and Holt, eds.), Williams & Wilkins Co., Baltimore) section 13.
Saito (1973), Arch. of Biochem. & Biophys. 155: 290–298.
Yuuki et al. (1985), J. Biochem. 98: 1147–1156.
Katz & Demain (1977), Bacteriol. Rev. 41: 449–474.
Dommergues et al. (1979), Appl. Environ. Microbiol., 37: 779–81.
Mugnier et al. (1985), Appl. Environ. Microbiol., 50: 108–114.
Bashan (1986), Appl. Environ. Microbiol., 51: 1089–1098.
Fages (1990), Appl. Microbiol. Biotechnol., 32: 473–478.
McKeen et al. (1986), Phytopathology, 76: 136–139.
Besson & Michel (1991), Microbios., 65: 15–21.

*Primary Examiner*—Michael G. Wityshyn
*Assistant Examiner*—Kristin K. Larson
*Attorney, Agent, or Firm*—Dann, Dorfman, Herrell and Skillman

[57] ABSTRACT

A *Bacillus licheniformis* producing an antifungal principle active against a wide variety of plant pathogenic fungi has been isolated. The microorganism was obtained from the rhizosphere of perennial ryegrass (Lolium perenne L.). The type isolate, strain PR1-36a, is particularly antagonistic to filamentous fungi, including Rhizoctonia and Magnaporthe. The microorganism was shown to be effective as a biocontrol agent for control of Fusarium seedling blight in corn. The antifungal principle produced by the microorganism is diffusible and may be purified by acid precipitation of the culture fluid, followed by ethanol extraction. The antifungal principle is fungistatic against several diverse species of fungi, and shows particularly strong activity against filamentous fungi, many of which are serious plant pathogens. Methods are provided for producing and using antifungal strains of *Bacillus licheniformis*, and antifungal principles produced therefrom, in treatment of soils, planting media, seeds and plant parts for control of various fungal plant diseases.

12 Claims, 7 Drawing Sheets

BACILLUS LICHENIFORMIS PRODUCING ANTIFUNGAL AGENTS AND USES THEREOF FOR CONTROL OF PHYTOPATHOGENIC FUNGI

FIELD OF THE INVENTION

This invention relates to the control of fungal diseases of plants, and more specifically to strains of *Bacillus licheniformis* producing antifungal compounds and uses thereof for controlling a wide variety of phytopathogenic fungi in soils, on seed and on plants of agronomic importance.

BACKGROUND OF THE INVENTION

Rhizobacteria have long been known for their role in promotion of plant growth and biological control of plant pathogenic microorganisms. It is believed that plant growth-promoting rhizobacteria act by displacing or antagonizing plant pathogenic microorganisms. Many of these rhizobacteria produce antibiotics, the production of which is strongly correlated with inhibition of various pathogenic microorganisms in vitro and disease suppression in vivo.

Various microorganisms in soil, including *Enterobacter aerogenes*, *Pseudomonas fluorescens*, *Pseudomonas cepacia*, and Bacillus species, have been reported to produce antibiotics and antifungal compounds that effectively control or suppress phytopathogenic fungi both in vitro and in vivo. Bacteria of the genus Bacillus produce a variety of peptide antibiotics that are antibacterial and/or antifungal. Several Bacillus species, including *B. subtilis*, *B. pumilus* and *B. cereus*, have been shown to be antagonistic to plant pathogenic fungi and bacteria. For example, phytopathogen-antagonistic strains of *B. subtilis* have been reported to produce two peptide antibiotics: bacilysin, a dipeptide that inhibits yeast and bacteria; and fengycin (fengymycin), a lipopeptide antagonistic against phytopathogenic fungi such as *Rhizoctonia solani*. (Loeffler et al. (1986), J. Phytopathology 115: 204–213; Vanittanakom et al. (1986), J. Antibiotics 39: 888–901). *Bacillus cereus* produces mycocerein, another antifungal peptide (Wakayama et al. (1984), Antimicrobial Agents and Chemotherapy 26: 939–940). Additionally, biological control of Eutypa lata on grapevine by an antagonistic strain of *Bacillus subtilis* has been reported (Ferreira et al. (1991), J. Phytopathology 81: 283–287) In that instance, inhibition of mycelial growth and ascospore germination was correlated with the presence of an antibiotic substance in an ethanol extract of the B. subtilis strain.

The Bacillus genus is divided into three groups, for purposes of identifying and classifying Bacillus species (Claus & Berkeley (1986) "Genus Bacillus Cohn 1872 174$^{AL}$", pp. 1104–1139 in *Bergey's Manual of Systematic Bacteriology*, Volume II (Sneath, Mair, Sharpe and Holt, eds.), Williams & Wilkins Co., Baltimore). Most Bacillus species reported to be useful as biological control agents belong to the "subtilis" group; which includes *B. subtilis*, *B. cereus*, *B. pumilus* and *B. licheniformis*, among others. Of this group, *Bacillus licheniformis* is industrially valuable for its ability to produce secreted products, such as thermally stable alpha amylases (See, e.g., Saito (1973), Arch. of Biochem. & Biophys. 155: 290–298; Yuuki et al. (1985), J. Biochem. 98: 1147–1156). Moreover, *Bacillus licheniformis* is known for its ability to survive and proliferate in extreme environments, including high temperature and anaerobic conditions (*B. licheniformis* is a facultative anaerobe). *Bacillus licheniformis* is widely known to produce antibiotics such as bacillomycin, bacitracin, licheniformin and proticin (See Katz & Demain (1977), Bacteriol. Rev. 41: 449–474). However, the ability of this species to produce antifungal compounds, as well as its usefulness as a biological agent for the control of plant diseases, has remained largely unexplored (See Loeffler et al. 1986, supra.).

Because *Bacillus licheniformis* can grow anaerobically and at elevated temperatures, it is capable of inhabiting a wide variety of rhizospheres, including waterlogged soils and/or soils exposed to extremes of heat, such as in semi-arid or arid regions, or tropical and sub-tropical areas. For this reason, it would be advantageous to identify strains of *Bacillus licheniformis* that are antagonistic to plant pathogenic fungi and that produce antifungal compounds. It would be a further advantage to identify such *Bacillus licheniformis* strains having an antagonistic effect on a wide variety of phytopathogenic fungi. Such organisms could be used for biological control of fungal plant pathogens on a broad range of plant species, against a large variety of pathogens. Insofar as is known, *Bacillus licheniformis* strains having such characteristics have heretofore not been identified.

SUMMARY OF THE INVENTION

One object of the present invention is to provide a microorganism having the identifying features of *Bacillus licheniformis*, which is antagonistic to a wide variety of fungal species, for use as a biological control agent of fungal plant diseases on horticulturally and agronomically important plants. According to one aspect of the present invention, a microorganism having the identifying features of *Bacillus licheniformis*, which is antagonistic to plant-colonizing fungi and which produces at least one antifungal compound, is provided for use in the biological control of phytopathogenic fungi on seeds and plants. In a preferred embodiment, this microorganism possesses the identifying characteristics of *Bacillus licheniformis* strain PR1-36a. *Bacillus licheniformis* strain PR1-36a produces an antifungal principle that is active against a diverse array of fungal species.

Another object of the present invention is to provide an antifungal principle produced by fungal-antagonistic strains of *Bacillus licheniformis*, for use in control of fungal plant diseases. According to another aspect of the present invention, an antifungal principle is provided, which is obtained from *Bacillus licheniformis*, preferably *B. licheniformis* strain PR1-36a. This antifungal substance comprises one or more active components which exhibit antifungal effects on plant-colonizing fungal species.

In accordance with another aspect of the present invention, methods are provided for producing microbial inoculants comprising fungal-antagonistic strains of *Bacillus licheniformis*, preferably strain PR1-36a. Methods are also provided for using such microbial inoculants for biological control of one or more fungal plant diseases.

According to yet another aspect of the present invention, methods are provided for producing an antifungal principle from fungal-antagonistic strains of *Bacillus licheniformis*, preferably *B. licheniformis* strain PR1-36a. Methods are also provided for using such antifungal principles for the control of fungal plant diseases.

The use of antifungal compound-producing *Bacillus licheniformis* strains for control of fungal plant diseases provides numerous advantages with respect to other antifungal bacterial inocula currently available. The ability of *Bacillus licheniformis* to grow anaerobically and at elevated temperatures, as well as its ability to form desiccation-resistant endospores, enable this bacterium to be used as an inoculant in a wide variety of environmental conditions. The diffusibility of the antifungal principle produced by *Bacillus licheniformis* contributes to its ease of purification, which is an additional advantage of *B. licheniformis* over other microbial inoculants. Furthermore, the antifungal principle is stable for long periods of time, which is yet another advantage of the antifungal *Bacillus licheniformis* strains of the present invention.

BRIEF DESCRIPTION OF THE DRAWINGS

FIG. 2: NMR spectra of ninhydrin-positive band (Rf value=0.46 cm) resolved by thin-layer chromatography (TLC) of ethanolic extract from *B. licheniformis* strain PR1-36a culture fluid. Solvent system for TLC: chloroform:methanol:water (65:25:4).

DETAILED DESCRIPTION OF THE INVENTION

Figure 1:
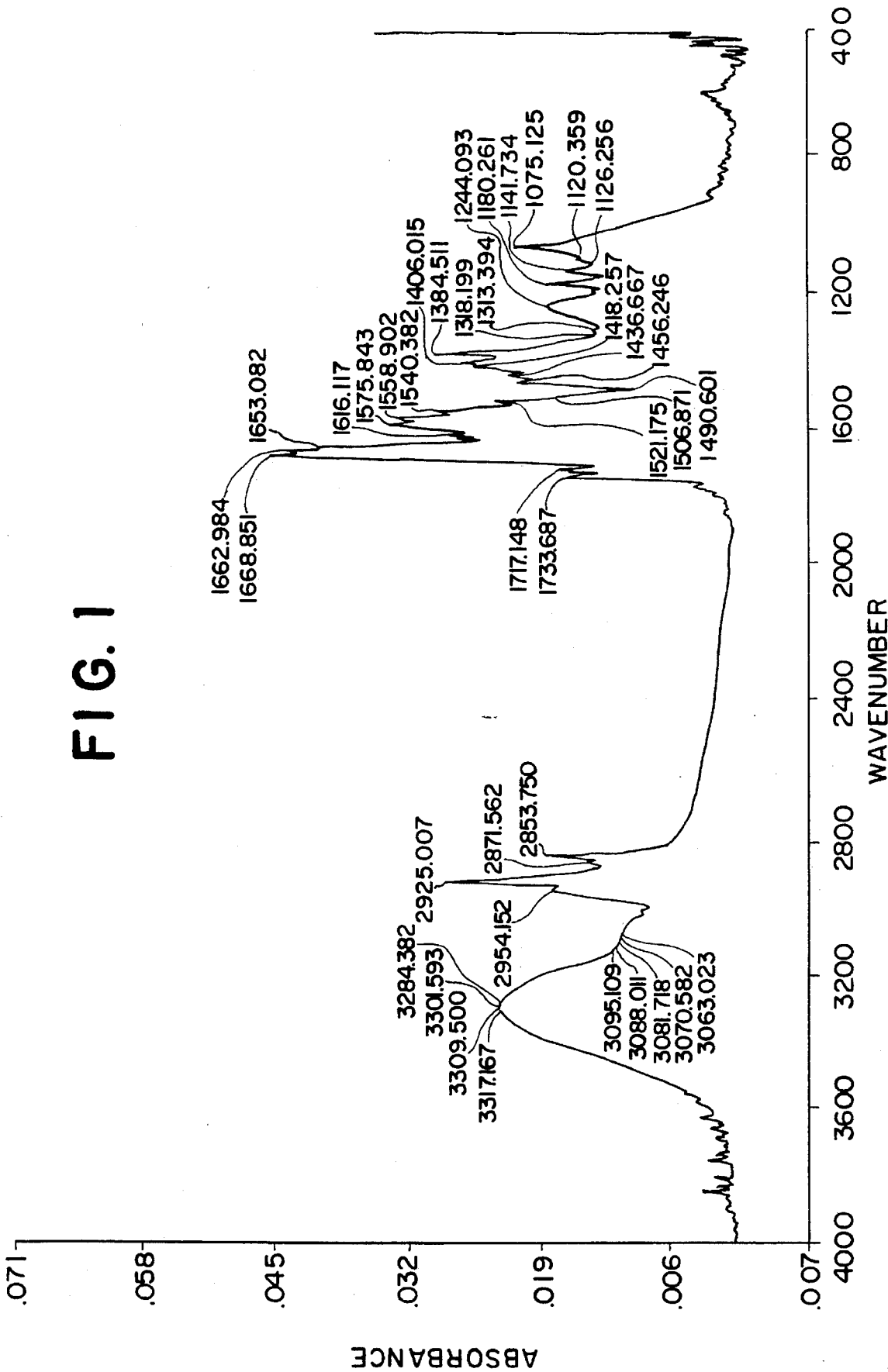
FIG. 1: IR spectrum of ninhydrin-positive band (Rf value=0.46 cm) resolved by thin-layer chromatography (TLC) of ethanolic extract from *B. licheniformis* strain PR1-36a culture fluid. Solvent system for TLC: chloroform:methanol:water (65:25:4). X axis=wavenumber ($cm^{-1}$); Y axis=absorbance.

It has been discovered in accordance with the present invention that a microorganism, identified as *Bacillus licheniformis*, is antagonistic to a variety of plant pathogenic fungi, including several common pathogens of turf grass and other graminaceous crops, such as corn (*Zea mays* L.). It has further been discovered in accordance with the present invention that *Bacillus licheniformis* appears to exert its antagonistic effect by producing one or more substances having antifungal activity. Insofar as is known, *Bacillus licheniformis* strains producing substances antagonistic to phytopathogenic fungi have not been identified.

The detailed description and examples set forth herein-below describe the isolation, identification and characterization of a *Bacillus licheniformis* strain, PR1-36a, which is antagonistic to various soil-borne plant pathogenic fungi and which produces one or more antifungal principles against a broad spectrum of plant- and rhizosphere-associated fungi. The term "antagonistic" as used herein refers broadly to the ability of one organism to negatively affect another organism, by mechanisms including, but not limited to, inhibiting growth of that organism, competing for nutrients, producing toxic substances and/or physical displacement of the organism. The antifungal principle is also described and exemplified hereinbelow. The antifungal principle may comprise one or more components. Hence, to the extent the terms "antifungal principle, agent or compound" are used herein, they refer to the plural as well as the singular. The term "antifungal" as used herein refers broadly to the ability of an organism or agent to exert an inhibitory effect on a fungus. Such an effect may be classified as fungicidal, fungistatic, sporocidal, sporostatic, or a combination thereof.

Although the PR1-36a isolate of *Bacillus licheniformis* is described and exemplified herein, such description is for the purpose of illustration, and is not intended to limit the invention to that strain. It will be appreciated by those skilled in the art that similar strains of *B. licheniformis* having the identifying characteristics and antifungal properties described for PR1-36a may be isolated and purified from the rhizosphere of various plant species, according to the methods set forth herein by which strain PR1-36a was obtained. *Bacillus licheniformis* strain PR1-36a was isolated from a rhizosphere of perennial ryegrass (*Lolium perenne* L.). The isolation of antifungal bacterial species from this rhizosphere and the purification and classification of *B. licheniformis* strain PR1-36a is described in detail in Example 1. As described in Example 1, isolate PR1-36a was identified as an endospore forming *Bacillus licheniformis* strain able to grow aerobically at 50° C. and anaerobically at 37° C.

*B. licheniformis* strain PR1-36a exhibited strong antagonism against filamentous fungi such as *Rhizoctonia solani* and *Magnaporthe poae* (see Example 1). Furthermore, imbibing corn kernels with *B. licheniformis* strain PR1-36a and sowing them in sand amended with inoculum of the corn pathogen, Fusarium roseum, resulting in the suppression of Fusarium seedling blight in controlled environmental chambers.

*B. licheniformis* strain PR1-36a produces a diffusible antifungal principle that can be obtained by acid precipitation of the culture filtrate followed by ethanol extraction, as described in detail in Example 2 herein. A crude ethanolic extract (CEE) prepared from culture filtrates of the bacterium was found to be fungistatic against a broad spectrum of phytopathogenic fungi (See Table 3 of Example 2), particularly filamentous fungi, causing malformation and swelling of the mycelium. The CEE was stable at room temperature for more than six months. The extract was resolved by thin-layer chromatography (TLC) into one ninhydrin-positive band whose Rf value was 0.79 in an ethanol:water (2:1) solvent system. Using another solvent system, the CEE was resolved by thin-layer chromatography into four biologically active ninhydrin-positive bands, having Rf values of 0.18, 0.21, 0.45 and 0.48. These ninhydrin-positive bands were all tested to be antifungal against *Fusarium moniliforme, Aspergillus niger, Rhizoctonia solani, Magnaporthe poae* and *Diplodia maydis*.

The biologically active ninhydrin-positive band having an Rf value of 0.46 in the chloroform:methanol:water (65:24:4) solvent system was analyzed by infrared (IR) spectroscopy and nuclear magnetic resonance (NMR) spectroscopy, as described in Example 2 herein. Both analyses suggest that the compound associated with this band comprises a short peptide (4–6 amino acid residues), and a lipid component. As described in the Background section above, peptide-containing antibacterial and antifungal substances have been isolated from other species of Bacillus. One of these, fengycin has also been reported to possess a lipid component (Vanittanakom et al., 1986, supra). The analysis of the crude ethanolic extract from *Bacillus licheniformis* strain PR1-36a suggests that *Bacillus licheniformis* also contains one or more such peptide- and/or lipid-containing compounds, and that at least one of these compounds, or a combination thereof, is fungistatic against numerous filamentous and other phytopathogenic fungi.

*Bacillus licheniformis* is considered an innocuous rhizosphere microorganism whose presence in conjunction with various grasses and crop species is either non-deleterious or beneficial. Accordingly, the *B. licheniformis* strain PR1-36a described herein also demonstrated no phytotoxic properties, but instead has been found to be a plant growth promoting organism. This plant growth promoting ability may be due in part to its ability to protect seeds and plants from fungal colonization. For example, corn seeds inoculated with strain PR1-36a were protected from Fusarium blight when tested in a controlled environment (see Example 2).

The *Bacillus licheniformis* described herein demonstrates several desirable physiological properties, such as the ability to grow anaerobically and/or at elevated temperature, production of desiccation-resistant endospores, rapid growth rates in common media, plant growth promoting capabilities and production of antifungal substances against common phytopathogens, particularly those causing diseases in turf grasses and other cereal crops, such as corn. All of these properties render this microorganism very suitable for use as a biological control agent for plant diseases of many types, under a variety of environmental settings and constraints.

To prepare the *Bacillus licheniformis* of the invention for use as a biological control agent, the microorganism is grown to stationary phase in a defined medium that favors the production of the antifungal substance or substances. An example of a suitable culture medium for growing the microorganisms of the invention is set forth in Example 2. Other suitable growth media will be readily apparent to those of skill in the art. Cultures may be grown in batch culture as described in Example 2, or the culture may be scaled up and performed in small or large fermentors, according to standard methods.

After growth to stationary phase (e.g., 3 days growth) cells are separated from the medium by centrifugation, and a bacterial pellet is harvested, which contains a mixture of spores and vegetative cells. The pellet can be resuspended in a liquid medium for use as a source of bacterial inoculum, or may be otherwise prepared for storage or mixing with soil and planting media. Inocula comprising antifungal *Bacillus licheniformis* strain prepared as described above may be further prepared in a variety of ways for delivery to crop plants for which biological control of one or more fungal diseases is desired. In a preferred embodiment, consistent dosage and viability of the *B. licheniformis* inoculum is achieved by entrapping bacterial cells and endospores in various biopolymers, such as polyacrylamide, xanthan or carob gums, or alginate, according to known methods (see, e.g., Dommergues et al., Appl. Environ. Microbiol., 37: 779–81, 1979; Mugnier et al., Appl. Environ. Microbiol., 50: 108–114, 1985; Bashan, Appl. Environ. Microbiol., 51: 1089–1098, 1986; and Fages, Appl. Microbiol. Biotechnol., 32: 473–478, 1990).

In another preferred embodiment, the viability and stability of a microbial inoculant comprising the *B. licheniformis* of the invention is improved by entrapping the Bacillus in the biopolymer matrix produced by flocculating rhizobacterial species, such as Azospirillum or Rhizobium. A method of producing a microbial inoculant for delivery of agriculturally beneficial microorganisms, such as the *Bacillus licheniformis* of the invention, as a co-flocculent with another flocculating bacterium, such as Azospirillum or Rhizobium is described in detail in co-pending U.S. application Ser. No. 08/024,328, which is incorporated by reference herein, in its entirety and is also described briefly below.

According to the methods described in U.S. application Ser. No. 08/024,328, a microbial inoculum comprising a flocculated form of bacterium, such as Azospirillum or Rhizobium, in which is entrapped another agriculturally beneficial microorganism such as the *Bacillus licheniformis* of the invention, is prepared as follows. A liquid growth medium (flocculation growth medium) is prepared, containing minimal salts medium, 8 mM fructose and 0.5 mM $KNO_3$. The minimal salts medium contains the following ingredients: 0.2 g/l $MgSO_4 \cdot 7\ H_2O$; 0.1 g/l NaCl; 0.02 g/l $CaCl_2$; 0.06 g/l Fe(EDTA); 0.02 g/l $Na_2MoO_4 \cdot 2\ H_2O$; 0.01 g/l $MnSO_4 \cdot H_2O$; 4.9 g/l KOH; 5.0 g/l malic acid; 0.02 g/l yeast extract (Difco) in a 10 mM phosphate buffer, final pH adjusted to 6.8. Pre-inocula of the flocculating bacterium (e.g., *Azospirillum brasilense*) are harvested from log-phase cultures grown in nutrient broth (NB, Difco, comprising peptone and beef extract having a low C:N ratio), and inoculated into the flocculation growth medium. At the same time, pre-inocula of *B. licheniformis* is inoculated into the flocculation growth medium. Cultures are incubated at 25°–37° C. and harvested after overnight (or longer) incubation. After such time, Azospirillum shift from a vegetative growth state to the flocculating physiology forming large macroscopic flocs in which the other microorganism, *B. licheniformis*, is entrapped. Co-flocs of the flocculating bacterium containing *B. licheniformis* are easily harvested by decanting the culture medium from flocs, which have settled to the bottom of the culture container. Such flocs may thereafter be stored or used as wet flocs, or may be dried, e.g., by air drying. Alternatively, culture medium may be removed from the co-flocs by coarse filtration methods and thereafter used or stored as wet flocs, or dried.

In an alternative embodiment, additional microorganisms, such as the *B. licheniformis* of the invention, may be mixed with the flocculating bacterium subsequent to the flocculation step. In inoculum produced in this manner, the additional microorganisms are not as securely entrapped in the biopolymer matrix of the flocculated bacteria; hence, the co-flocculation procedure described above is preferred.

Flocculated inocula comprising *B. licheniformis* provide a high-density inoculum containing $10^{11}$–$10^{12}$ cell/gm of floc. These inocula may be stored for long periods of time with no appreciable loss of cell viability.

Application of microbial inoculants comprising the antifungal *Bacillus licheniformis* of the invention for biological control of plant pathogens includes several simple techniques, such as coating seeds with the inoculant, mixing the inoculant into soil or germination media and spraying the inoculant onto various portions of plants. Such methods are familiar to agronomists and do not call for sophistication in processing and equipment.

In a preferred embodiment, seeds are coated with a microbial inoculant comprising *B. licheniformis* for the purpose of controlling seed-borne fungal pathogens during germination and seedling development and also for the purpose of extending the storage life of seeds. In this regard, it will be appreciated that the application of the *B. licheniformis* strains of the invention to seed is useful as a general seed cleaning method, by which to control seed-borne fungi that are not only plant pathogenic, but which may be toxic to livestock consuming such seed as feed (e.g., toxin-producing fungi such as those producing aflatoxins).

Seeds may be treated with the *B. licheniformis* of the invention by dipping them directly into a solution containing the microorganism (concentration of $10^7$–$10^8$ cells/ml) or by otherwise coating the seeds with the microorganism. Such coating may be facilitated by providing additives to the microbial inoculant, such as various adhesives, or by providing the inoculant as a co-flocculent with a flocculating bacterium as described above.

A microbial inoculant comprising *B. licheniformis* may also be used to inoculate planting media, such as soil, potting mixtures, or other germination mixtures prior to planting seeds. This is accomplished by mixing the inoculum with planting mixtures or by tilling the inoculum into field soils, either alone or along with fertilizers or other pre-planting soil treatments. Such methods are well known to agronomists.

A microbial inoculant comprising the *B. licheniformis* of the invention may also be applied to selected portions of plants to control fungal plant disease. For example, inoculants may be sprayed on the leaf portions of turf grass sod to control various fungal diseases or turf grass. Other methods of applying a microbial inoculant comprising the *B. licheniformis* of the invention for control of various plant diseases will be apparent to those of skill in the art.

*Bacillus licheniformis* strain PR1-36a was found to be an effective antagonist against a wide variety of fungi, including several fungal species that cause diseases of turf grass and cereal crop which can lead to significant economic loss. Accordingly, *Bacillus licheniformis* strains such as PR1-36a, which produce broad-spectrum antifungal compounds, are contemplated for use in control of a wide variety of economically significant phytopathogenic fungi of turf grass, cereal crops and other graminacious species. Moreover, to the extent that certain fungal pathogens against which *B. licheniformis* is active (e.g., Fusarium) are also known to produce disease on other non-grass crop species (e.g., tomato), the *Bacillus licheniformis* strains of the invention are also contemplated for utility in biological control of those diseases. Fungi that may be biologically controlled by antifungal compound-producing *B. licheniformis* strains of the invention include, but are not limited to: Alternaria spp., Aspergillus spp. (e.g., *A. flavus, A. niger*), Curvularia spp., *Diplodia maydis*, Fusarium spp. (including *F. moniliforme, F. oxysporum, F. roseum*), Helminthosporeum spp. (including *H. maydis*), Magnaporthe poae, Penicillium spp., Rhizopus spp., and Rhizoctonia solani. Plant or crop species that may be biologically protected by the *B. licheniformis* strains of the invention include, but are not limited to: (1) turf grasses and field grasses, such as perennial ryegrass, bluegrass, rescue, and bent grass, among others; (2) cereal crop species, such as corn, sorghum, rice, wheat, rye, millet and barley; (3) broadleaf crops, such as soybeans, alfalfa, beans, peanuts, cotton, tobacco and potato; and (4) vegetable and floral crops, such as tomatoes, cucumbers, peppers, beets, carrots and roses.

As discussed above, the ethanolic extract of *B. licheniformis* strain PR1-36a culture filtrate, which contained the antifungal principles, was found to be active against numerous filamentous fungi and retained activity for several months. Accordingly, the active antifungal principles of the *B. licheniformis* strains of the invention may also be utilized for control of such fungal plant pathogens, thereby improving health, promoting growth and increasing yield of horticulturally and agronomically important plants. The antifungal principle may be isolated from cultures of *Bacillus licheniformis* strains such as PR1-36a, according to known methods, such as those described by McKeen et al. (1986), Phytopathology, 76: 135–139, and described in detail in Example 2 herein. The one or more antifungal principles present in such an ethanolic extract may be used without further separation in formulations for pest control, according to standard methods. Concentrations of the antifungal principle suitable for obtaining a fungistatic effect fall in the range of 10–50 µg of evaporated ethanol extract per ml.

The antifungal principle may be formulated with any standard solvents, dispersion media, wetting agents, powders, grannules, etc., for application to soils and plant parts. To the extent they are compatible with the antifungal principle produced by the *B. licheniformis* of the invention, any and all such solvents and additives are contemplated for use in the practice of the invention. Furthermore, it is also understood that the antifungal principle present in the ethanolic extract described herein may be subjected to further treatment (e.g., removal of ethanol, lyophilization or other drying measures, etc.) to the extent that such additional treatments do not interfere with the activity of the antifungal principle or components thereof.

The antifungal principle in the ethanolic extract of *B. licheniformis* strains such as PR1-36a may also be subjected to further separation and purification according to standard methods. Such methods include, but are not limited to, various chromatography procedures, such as thin-layer chromatography, gas chromatography or high-performance liquid chromatography (HPLC), using standard preparative protocols. Individual components of the antifungal principle may then be used separately in formulation of liquid- or solid-based fungicides for control of plant colonizing fungi on a wide variety of plant species, as described hereinabove for microbial inoculants comprising *B. licheniformis* strains of the invention.

The present invention provides an antifungal compound-producing *Bacillus licheniformis* which is antagonistic against numerous soil-borne and/or plant pathogenic fungi. The type isolate, PR1-36a, possesses the typical characteristics of *B. licheniformis*, including endospore formation, aerobic growth at elevated temperatures and the ability to grow anaerobically. The *Bacillus licheniformis* of the invention produces a physiologically active agent, which is a diffusible antifungal principle obtainable by acid precipitation of the culture filtrate followed by ethanol extraction. The broad spectrum of antifungal activity against several agronomically important. phytopathogenic fungi renders antifungal compound-producing strains of *Bacillus licheniformis* particularly useful as biological control agents to reduce the impact of plant disease, thus improving seed germination, seedling establishment and plant growth. Because of the general effect on several diverse fungal species, filamentous fungi in particular, the use of this microorganism may be extended for the purpose of general seed cleaning to improve germination and/or to reduce the incidence of toxin-producing fungi which are detrimental to livestock consuming seeds of such crops. The ability of this microorganism to form spores, its thermophilicity and anaerobic growth capability render it extremely suitable for use under a variety of environmental settings. The diffusible nature of the antifungal principle enables easy purification of the active principle, and the stability of the antifungal principle provides a further advantage for production of chemical formulations for control of fungal plant pathogens.

The following examples are provided to describe the invention in further detail. These examples are intended merely to illustrate and not to limit the invention.

EXAMPLE 1

ISOLATION OF BACILLUS LICHENIFORMIS

STRAIN PR1-36a FROM TURF GRASS

In this example, a process is described for isolating and identifying bacterial species that show fungal-suppressive activities against plant pathogenic fungi of turf grass and other grass species. The procedure involves the isolation and culture of bacteria from the rhizosphere supporting the host plant species for which antifungal bacteria are desired. In the present case, a turf grass rhizosphere was selected.

MATERIALS AND METHODS

Fungal strains. Corn fungal pathogens were obtained from Dr. Loral Castor (Ciba-Geigy Seed Division, Bloomington, Ill.); Pythium sp. and Rhizoctonia sp. strains were obtained from Dr. Mitch White (Agri-Diagnostics Lab., Cinnaminson, N.J.) and Magnaporthe poae strains were provided by Dr. Bruce Clarke from the Plant Pathology Department, Rutgers University, New Brunswick, N.J.

Screening for antifungal bacteria. Seeds of perennial ryegrass (*Lolium perenne* L. cv Assure) were sown in pots containing a sandy-loam field soil collected from the Adelphia farm of the New Jersey Agricultural Experimental Station. Rhizosphere soil samples from this grass were serially diluted in water and plated on various specific and non-specific media to isolate bacteria showing potential for antifungal properties. The media used for the isolation were Plate Count Agar (PCA), Crystal Violet Nutrient Agar (CVA), King B agar for Pseudomonas spp. and MacConkey agar for Enterobacter spp. and were purchased from Difco Laboratories, Detroit, Mich.

Single colonies showing potential for antifungal activity were transferred to Potato Dextrose Agar (PDA). The ability of the isolates to inhibit known phytopathogenic fungi were tested. A loopful of bacterial isolates were placed on PDA plates containing actively growing mycelia of three different fungi, Magnaporthe poae, *Rhizoctonia solani* and *Pythium ultimum*, and were incubated at 30° C. for 1 week. The zones of inhibition caused by various isolates were indicative of antifungal activity and these isolates were later maintained on nutrient agar slants for further studies.

Strain identification. The endospore forming isolates were initially recognized as Bacillus spp. and were classified morphologically and biochemically in accordance with the Bergey's Manual of Systematic Bacteriology.

RESULTS

Isolation of antifungal bacteria. Screening for antifungal bacteria from the rhizosphere of perennial ryegrass, using various media, yielded several different classes of bacteria showing antagonism towards contaminating fungi on the plates. About 100 different bacterial isolates were obtained, of which 38% belonged to the endospore forming Bacillus spp., 18% were Pseudomonas spp. and 10% were Enterbacter spp. Since the Bacillus group was predominant in the rhizosphere tested, the study was initiated using the Bacillus isolates to determine the antifungal properties against three different known phytopathogens that affect turfgrasses. As shown in Table 1, twenty-eight isolates were strongly antagonistic against *R. solani* and *M. poae* but less effective against *P. ultimum*. Only five of the 33 bacillus isolates tested were ineffective against all three pathogens.

Strain identification and classification. Table 2 shows the morphological and biochemical tests performed on the isolates according to an established protocol for the identification of Bacillus species given in the Bergey's Manual of Systematic Bacteriology. All isolates were endospore forming, strongly catalase positive and VP positive and indicative of Bacillus spp. Isolate #PR1-36a was further characterized biochemically and it was able to grow at 50° C. aerobically and anaerobically at 37° C. Other properties included lysozyme sensitivity and inability for tyrosine degradation. Although it did not change the pH indicator color in the propionate utilization test, small colonies of the isolate did grow on the medium after 48 hours of incubation. Hence, according to the key, it was tentatively identified as *Bacillus licheniformis*. Our conclusion was later confirmed by the Bacillus Genetics Stock Center, Ohio State University, Columbus, Ohio. *Bacillus licheniforms* strain PR1-36a was deposited on Sep. 1, 1994 with the American Type Culture collection (Rockvlle, Md.) and assigned ATTCC accession number 55606.

TABLE 1

Antifungal activity of the Bacillus spp. isolates against three fungal pathogens *Rhizoctonia solani* AG4 *Pythium ultimum*, *Magnaporthe poae* NAVA on Potato Dextrose Agar

| Isolate No. | Rhizoctonia solani | Pythium ultimumi | Magnaporthe poae |
|---|---|---|---|
| PR1-1 | + | + | ++ |
| PR1-3a | +++ | + | +++ |
| PR1-4a | +++ | + | +++ |
| PR1-5 | + | + | + |
| PR1-6 | + | + | + |
| PR1-7 | − | − | − |
| PR1-9a | + | + | + |
| PR1-9b | + | − | + |
| PR1-10 | +++ | + | +++ |
| PR1-11a | + | − | + |
| PR1-12a | + | − | − |
| PR1-13 | +++ | + | +++ |
| PR1-20 | − | + | ++ |
| PR1-26a | +++ | ++ | +++ |
| PR1-27 | − | − | − |
| PR1-28 | − | − | + |
| PR1-32 | +++ | + | +++ |
| PR1-36a | +++ | + | +++ |
| PR1-37a | + | + | +++ |
| PR2-10 | +++ | + | +++ |
| PR2-11 | + | − | + |
| PR2-12 | ++ | + | + |
| PR2-13 | +++ | + | +++ |
| PR2-14 | − | − | + |
| PR2-15 | + | + | ++ |
| PR2-16 | − | − | + |
| PR2-17 | − | − | − |
| PR2-18 | − | − | + |
| PR2-20 | ++ | ++ | +++ |
| PR2-21 | − | + | + |
| PR2-22 | − | + | + |
| PR2-23 | − | − | − |
| PR2-24 | − | − | + |

−, no inhibition; +, poor inhibition; ++, good inhibition; +++, v. good inhibition.

TABLE 2

| Test Characteristics | Results |
|---|---|
| Gram Stain | + |
| Cell type | Rod |
| Motility | + |
| Colony morphology on NA | Rough, irregular, dry |
| Spores | + |
| ellipsoidal | − |
| swelling of sporangium | − |
| Unstained globules in protoplasm | + |
| Catalase | + |
| V-P reaction | + |
| Ph in V-P broth | 5.3–5.6 |
| Growth in anaerobic agar | + |
| in 7% NaCl | + |
| in media at pH 5.7 | + |
| at 50° C. | + |
| at 65° C. | − |
| Acid from glucose | + |
| Hydrolysis of starch | + |
| Use of citrate | + |
| Decomposition of casein | + |

TABLE 2-continued

| Test Characteristics | Results |
|---|---|
| Reduction of $NO_3$ to $NO_2$ | + |
| Antimicrobial production | + |

EXAMPLE 2

RECOVERY AND CHARACTERIZATION OF ANTIFUNGAL

SUBSTANCES FROM Bacillus Licheniformis STRAIN PR1-36a

In this Example we describe the recovery and physical characterization of antifungal substances from *B. licheniformis* strain PR1-36a. The range of antifungal activity of a crude ethanolic extract of these substances is also described.

MATERIALS AND METHODS

Growth and extraction of the antifungal compound(s). For the isolation and enrichment of the antifungal compound, the procedure described by Mckeen et al. (1986), Phytopathology 76: 135–139, was followed. The isolate PR1-36a was grown on nutrient agar slants 24 hrs. prior to transferring in the antibiotic production medium. The antibiotic medium contained 20 g of Difco-Bacto dextrose, 5 g of DL-glutamic acid, 1.02 g of $MgSO_4 7 H_1O$, 1 g of $K_2HPO_4$, 0.5 g of KCl, and 1 ml of trace element solution (0.5 g of $MnSO_4$, 0.16 g $CuSO_4 5 H_2O$, and 0.015 g of $FeSO_4 \cdot 7H_2O$ in 100 ml of water) per liter. The pH of the medium was adjusted to 6.0–6.5. The cultures were grown in batch cultures in 500 ml conical flasks containing 200 ml of the medium. After inoculation with 1 ml of the washing from the nutrient agar slant, the flasks were incubated at 30° C. in a gyrotory shaker, (New Brunswick Scientific), at a speed of 200 rpm for 3 days.

After 3 days of growth, the supernatant of the culture was obtained by centrifugation for 20 minutes at 16,500 g at 4° C. The antifungal compounds were precipitated by adjusting the pH to 2.5 with concentrated HCl. The precipitated material was later harvested by centrifugation for 10 minutes at 16,500 g. The pellet containing the active fraction was then suspended and extracted in 50 ml of 80% ethanol three times. The 80% ethanolic extract was later evaporated to dryness in a rotary evaporator at 55° C. The dried material designated as Crude Ethanol Extract (CEE), was stored in vials at room temperature as well as at 4° C. until further use.

Antimicrobial spectra of the crude ethanol extract. The antimicrobial activity of the CEE was performed on PDA plates for fungi and yeast. For testing of antibacterial and anti-yeast activity, Luria Bertani (LB) agar plates were used (Sambrook et al., *Molecular Cloning: A Laboratory Manual*, Cold Spring Harbor Laboratory, New York). The antimicrobial activity was determined by paper disc method in which 100 µg of the CEE were placed on sterile sensi-discs of 9.52 mm diameter (Schleicher & Schuell Inc., N.H.). The discs were placed on respective plates of actively growing fungal cultures. For antagonism against bacteria, the plates were spread with bacteria and immediately the discs impregnated with the CEE was placed and the plates were incubated at 30° C. for 2 to 7 days. Hyphal morphology of the mycelial mat from the CEE treatment were examined under microscope.

Minimum Inhibitory Concentration (MIC). Minimum inhibitory concentration of the CEE was determined by incorporating serial dilutions of CEE ranging from 10 ug per ml to 100 µg per ml in PDA. The plates were poured with different concentrations and plugs of mycelia from different test fungi were placed on the plates and incubated at 30° C. for two weeks. Fresh outgrowth from mycelial plug was assessed in the plates containing different concentrations of CEE.

Thin layer chromatography of the CEE. Several solvent systems (A: ethanol/water 2:1; B: chloroform 100%; C: chloroform/methanol/water 65:25:4; D: chloroform/methanol/water 2:2:1; and E: butanol/acetic acid/water 4:3:3) were used to determine the relative mobility of the antifungal compounds in ascending chromatographic technique, using pre-coated plates with 0.2 mm layer of silica gel 60-F 254 (Merck & Co., Rahway, N.J.). The bands were visualized by spraying the chromatogram with a 0.2% butanolic ninhydrin solution (Sigma Chemical Co.) and heating the plates at 100° C. for 5 minutes.

Bioautography. The chromatograms obtained after thin-layer chromatography of the CEE in chloroform/methanol/water (65:25:4) were included in malt agar seeded with *Aspergillus niger* as the sensitive organism. Plates were incubated for 2 days at 28° C., after which the presence of an active antifungal compound was detected by a zone of growth inhibition (method of Besson & Michel (1991), Microbios., 65: 15–21).

Spectroscopy. Infrared spectroscopy was performed according to established methods. Proton-and $^{13}C$-nuclear magnetic resonance spectroscopy were also performed according to standard methods.

Bioassay for seedling blight of corn. Sweet corn kernels obtained from Abbot and Cobb Co. (Seed Lot #60591 PKF) were imbibed in water (untreated control) and in aqueous suspension of *B. licheniformis* PR1-36a for 6 hours. *B. licheniformis* cells were harvested from tryptic soy broth culture grown overnight. Five seeds per treatment were used for testing the disease suppression in a controlled environmental chamber. Seeds were sown individually in 2" pots filled with sand mixed with soil in the ratio of 3:1. A 4 cm deep hole was made in each soil surface and 1 ml of a week old mycelial suspension of Fusarium roseum were pipetted into each hole and the holes were half filled with soil. One kernel was dropped into each hole and covered with soil. The experiment was conducted in a growth chamber set at 20° C.

RESULTS

Antimicrobial and chemical properties of the Crude Ethanolic Extract (CEE). Table 3 shows the antimicrobial spectrum of the CEE.

TABLE 3

Antifungal and Antimicrobial Activity of the Crude Ethanolic Extract from the *B. licheniformis* PR1-36a Isolate Against Various Turf and Corn Fungal Pathogens and Other Microorganisms

| Test Organism | Antifungal Activity |
|---|---|
| Fungi | |
| *Alternaria* spp.[a] | +++ |
| *Aspergillus flavus*[a]* | ++ |
| *Aspergillus niger*[a]* | ++ |
| *Curvularia* spp.[a] | ++ |
| *Diplodia maydis* | +++ |

TABLE 3-continued

Antifungal and Antimicrobial Activity of the
Crude Ethanolic Extract from the *B.
licheniformis* PR1-36a Isolate Against
Various Turf and Corn Fungal Pathogens
and Other Microorganisms

| Test Organism | Antifungal Activity |
| --- | --- |
| *Fusarium moniliforme* | ++ |
| *Fusarium oxysporum* | + |
| *Fusarium roseum* | ++ |
| *Helminthosporium* spp.[a] | ++ |
| *Helminthosporium maydis* | +++ |
| *Magnaporthe poae* | +++ |
| *Penicillium* spp.[a*] | – |
| *Pythium aphanidermatum* | – |
| *Rhizopus* spp.[a*] | +++ |
| *Rhizoctonia solani* | +++ |
| Bacteria | |
| E. coli | – |
| Azospirillum brasilense | – |
| Bacillus subtilis | – |
| Bacillus cereus | + |
| Yeast | |
| Saccharomyces cereviciae | – |

[a]Epiphytic isolate from the Kentucky Blue grass seeds.
[a*]Epiphytic isolate from corn seeds.
–, no inhibition; +, poor inhibition; ++ good inhibition; +++ v. good inhibition.

Several filamentous fungi known to be pathogenic to corn and turf grasses were particularly sensitive to the CEE, but the extract was not antibacterial or anti-yeast (Table 3). The extract was observed to be fungistatic but neither fungicidal nor sporicidal. Spores of Fusarium spp., Penicillium spp., Aspergillus spp. and Helminthosporium spp. were observed to germinate in the CEE containing medium. However, the newly germinated mycelium was abnormal when observed under phase contrast microscope. The fungal mycelium exposed to CEE were all malformed, stunted and swollen. Minimum Inhibitory Concentration of the extract varied for different fungal genera between 10 μg/ml to 40 μg/ml as shown in Table 4.

TABLE 4

Minimum Inhibitory Concentration* of the CEE
from *B. licheniformis* PR1-36a Isolate on
Filamentous Fungi

| Fungi | MIC (μg/ml) |
| --- | --- |
| *Diplodia maydis* | 20 |
| *Fusarium moniliforme* | 40 |
| *Fusarium roseum* | 40 |
| *Helminthosporium maydis* | 20 |
| *Magnaporthe pose* | 10 |
| *Rhizoctonia solani* | 40 |

*Tests were done using a concentration range of 10 to 100 μg/ml.

When the CEE was resolved by thin-layer chromatography (TLC), it separated into one biologically active ninhydrin-positive band with an Rf value of 0.79 in the ethanol:water (2:1) system, and four biologically active ninhydrin-positive bands with Rf values of 0.18, 0.21, 0.43, and 0.46 in the chloroform:methanol:water (65:25:4) system (Table 5). Ninhydrin-positive bands were all tested to be antifungal against *Fusarium moniliforme, Aspergillus niger, Rhizoctonia solani, Magnaporthe poae* and *Diplodiamaydis*.

TABLE 5

Silica Gel Thin-Layer Chromatographic Migration of
the Antifungal Compounds Produced by *Bacillus
licheniformis* PR1-36a

| Solvent system | $R_f$ Ninhydrin positive | Ninhydrin negative |
| --- | --- | --- |
| Ethanol:water (2:1) | 0.79 | 0.91 |
| Chloroform (100%) | nil | nil |
| Chloroform:Acetone (9:1) | nil | nil |
| Methanol (100%) | nil | nil |
| Chloroform:methanol:water (2:2:1) | 0.9 | 0.98 |
| Chloroform:methanol:water (65:24:4) | 0.18;0.21 0.43;0.46 | 0.30;0.37; 0.60;0.72; 0.83;0.93 |

Plant bioassay with *Bacillus licheniformis*. Coating of sweet corn, kentucky blue and ryegrass seeds with *B. licheniformis* PR1-36a did not affect germination or seedling growth which indicated the absence of phytopathogenic properties by this bacterium. An interesting observation was that many seeds from the lot of sweet corn were found to be naturally infested with several fungal pathogens of corn like *Fusarium roseum, Aspergillus niger, Aspergillus flavus*, Rhizopus spp., and Penicillium spp. as evidenced by their easy isolation as epiphytic population on regular PDA media. Accordingly, also tested the effectiveness of the isolate *B. licheniformis* PR1-36a for the control of seedling blight of corn caused by Fusarium roseum. The bacteria-imbibed and water-imbibed seeds were planted in sand:soil mixture with and without externally added *Fusarium roseum* mycelial suspensions. The water-imbibed seedlings were seriously infected with *Fusarium roseum* and as a result the hypocytyl and seed coated were weak and turned deep red due to fungal infection while the bacteria-imbibed seeds were not affected by the fungus and the 10 day old seedlings showed healthy and well formed root system.

Physico-Chemical Characterization of One Component of the Antifungal Principle. The biologically active ninhydrin-positive band having an Rf value of 0.46 in the chloroform:methanol:water (65:25:4) system (hereinafter referred to as the "0.46 Rf component"; see Table 5) was further analyzed by infrared spectroscopy and by $^1$H and $^{13}$C nuclear magnetic resonance spectroscopy.

The IR spectrum of the 0.46 Rf component is shown in FIG. 1. The IR spectrum indicates that the compound associated with this component comprises a peptide, as reflected by the bands at 3,400 cm$^{-1}$ for amino- and hydroxyl-groups of amino acids, as well as a pair of strong bands at 1,650 and 1,520 cm$^{-1}$, indicative of a peptide bond. Furthermore, the bands appearing at about 2,800–3,000 cm$^{-1}$ are indicative of aliphatic side chains, which could be associated with amino acid residues or with lipids. Other functionalities indicated by the IR spectrum include the presence of an aromatic group, possibly associated with a tyrosine residue.

The solubility of the 0.46 Rf component in methanol suggests that the material is a low- to medium-molecular weight species (<1,000 daltons).

Figure 2A:
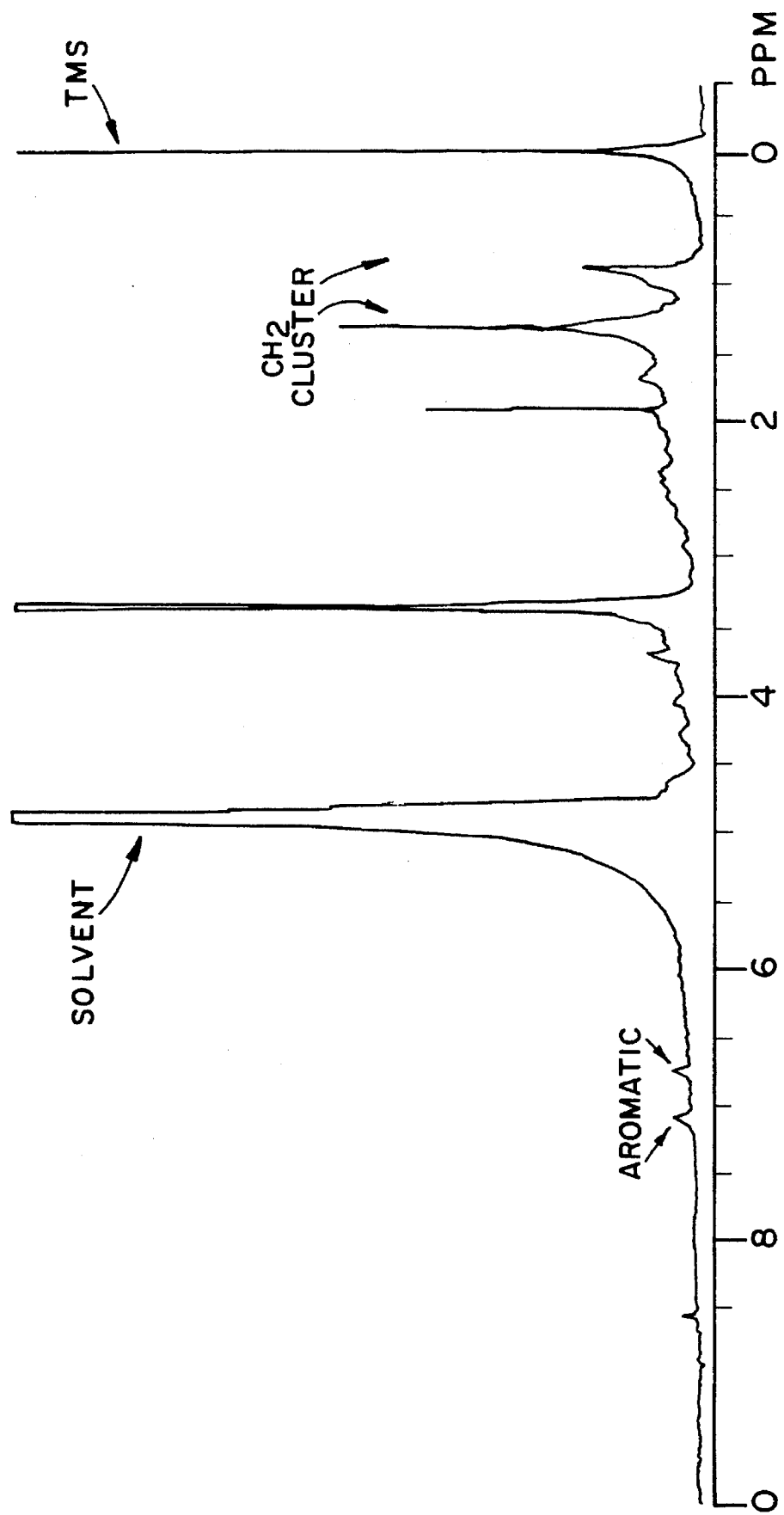
FIG. 2A: Proton ($^1H$) NMR spectrum (inset is expanded view of portion of larger spectrum).
Figure 2B:
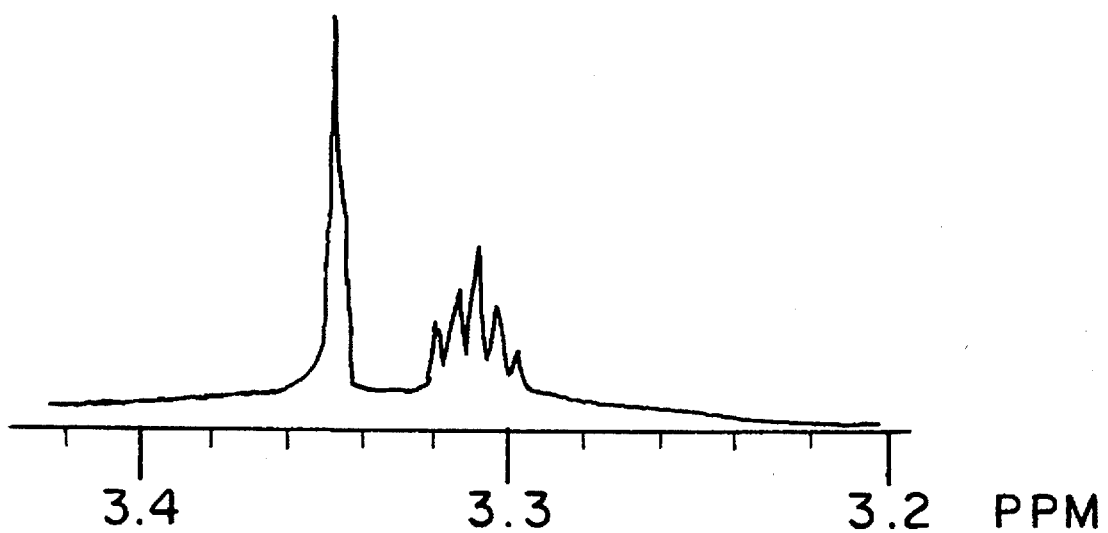
FIG. 2B: carbon ($^{13}C$) NMR spectrum. From top to bottom: 0–200 PPM; 60–180 PPM; 100–180 PPM; 28–32 PPM.
Figure 3A:
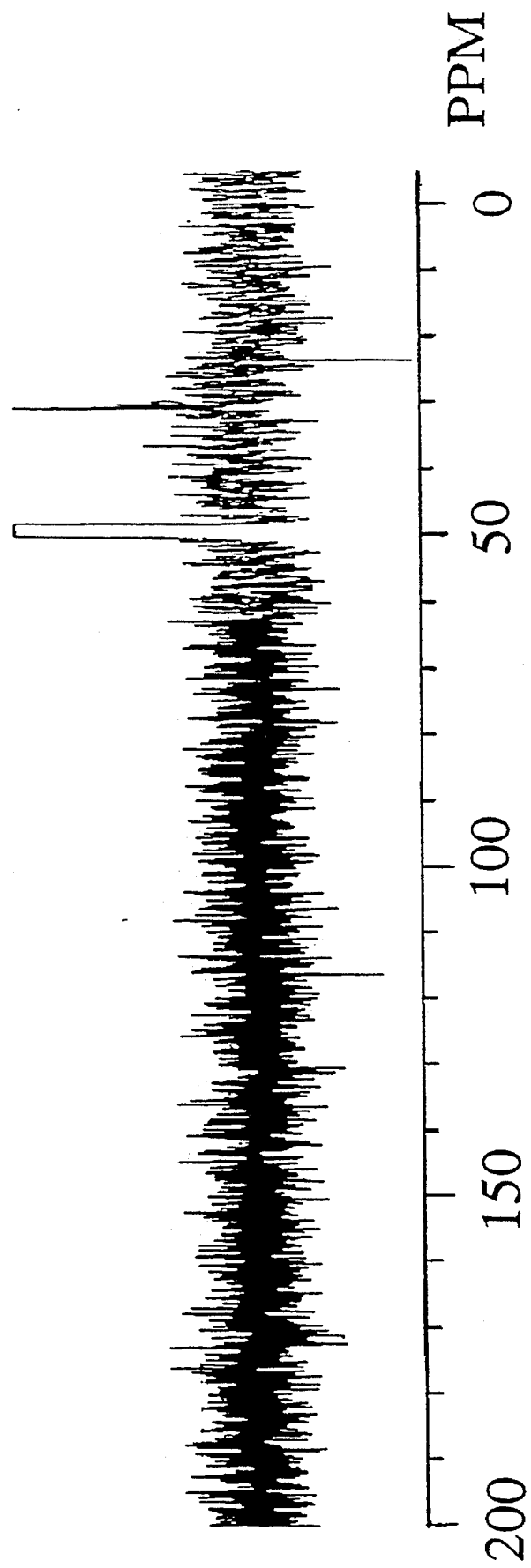
Figure 3B:
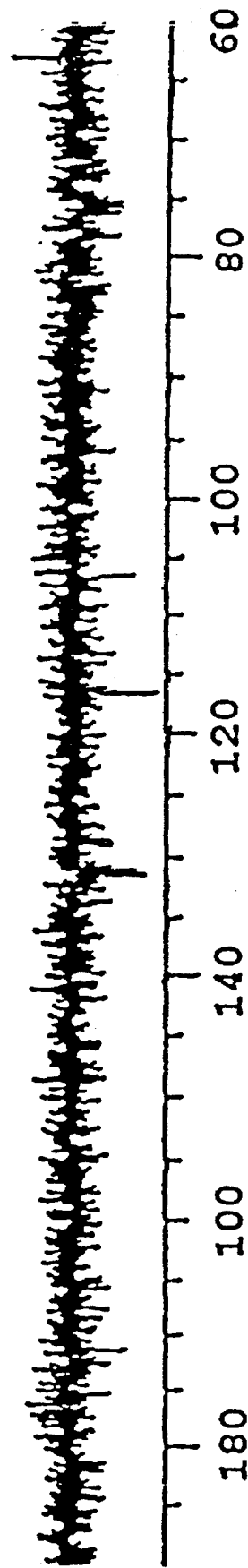
Figure 3C:
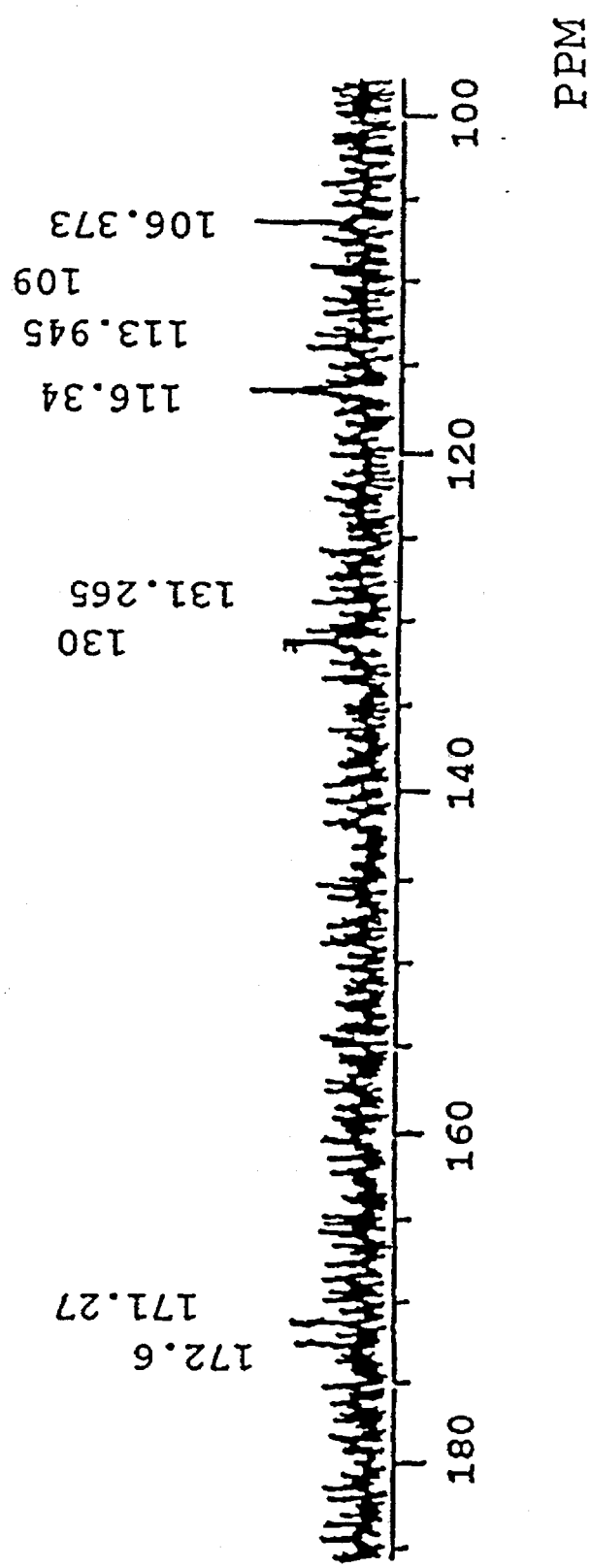
Figure 3D:
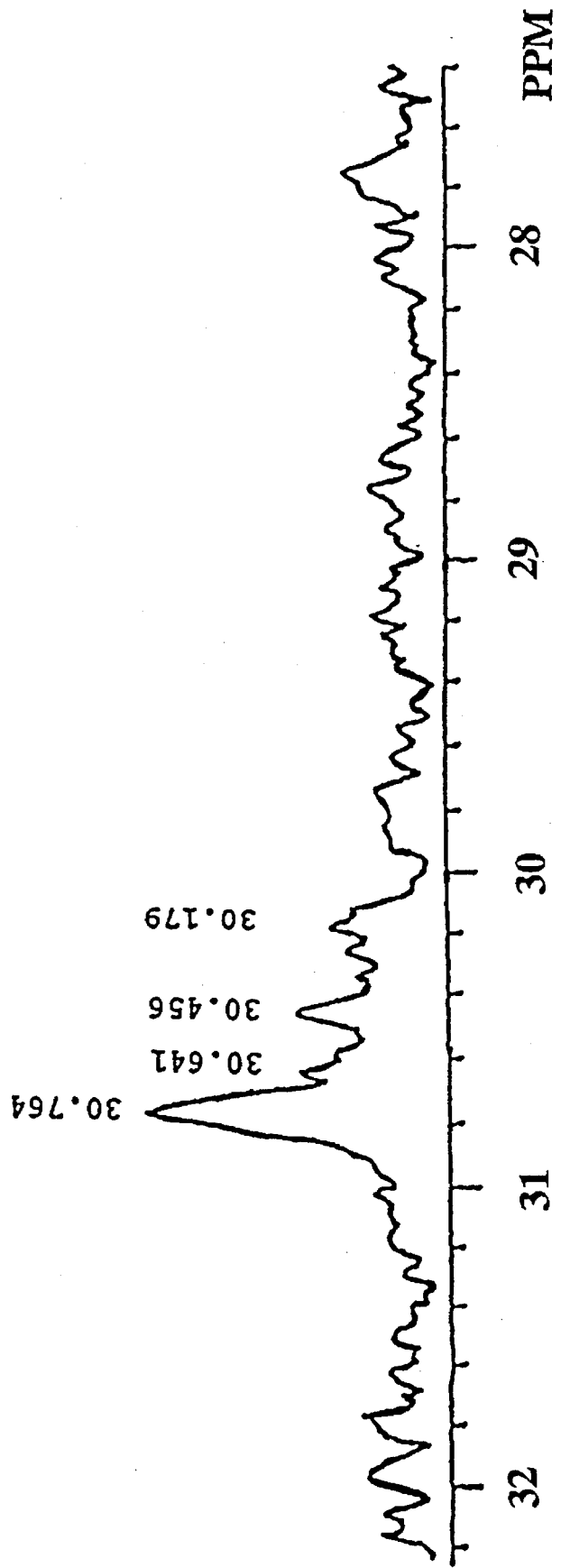

The $^1$H and $^{13}$C NMR spectra obtained for the 0.46 Rf component are shown in FIG. 2. These spectra indicate that the component contains a lipid moiety, as reflected by a close aggregation of CH$_2$ groups. The NMR spectra also indicate that the compound contains a peptide moiety in which the peptide chain is probably short (i.e., approx. 4–6 amino acids). Additionally, as indicated by the $^1$H NMR (which shows a pair of symmetrically coupling aromatic protons) and the $^{13}C$ NMR (which shows at least one peak characteristic of a tyrosine residue), one of the amino acid residues of the peptide may be tyrosine.

Thus, according to the analyses described above, the 0.46 Rf component of the CEE appears to comprise a lipopeptide. The peptide moiety is relatively short, and the molecular weight of the entire component is probably low.

Certain preferred embodiments have been specifically described and exemplified above. However, the present invention is not limited to those specific embodiments, but is capable of variation and modification without departure from the scope of the appended claims.

What is claimed is:

1. A method for biologically controlling a plant disease caused by a plant-colonizing fungus, which comprises inoculating a plant requiring disease control with an effective amount of a microbial inoculant comprising a microorganism having all of the identifying characteristics of *Bacillus licheniformis* strain PR1-36a, said inoculation resulting in the control of said plant disease.

2. A method according to claim 1, wherein said inoculation results in the control of more than one plant disease.

3. The method according to claim 1, wherein said plant is inoculated by coating seeds of said plant with said microbial inoculant.

4. The method according to claim 1, wherein said plant is inoculated by mixing said microbial inoculant with a growth medium in which said plant is growing.

5. The method according to claim 1, wherein said plant is inoculated by mixing said microbial inoculant with a planting medium in which seeds of said plant are germinated.

6. The method according to claim 1, wherein said plant is inoculated by applying said microbial inoculant to aboveground portions of said plant.

7. The method according to claim 1, wherein said plant is selected from the group consisting of turf grasses, field grasses and cereal crops.

8. The method according to claim 7, wherein said plant is corn and said plant disease is seedling blight.

9. The method according to claim 1, wherein said plant is inoculated by applying said microbial inoculant to said plant.

10. A microbial inoculant for controlling a plant disease caused by a plant colonizing fungus, which comprises a microorganism having all of the identifying characteristics of *Bacillus licheniforis* strain PR1-36a.

11. A biologically pure culture of a microoganism having all of the identifying characteristics of *Bacillus licheniformis* strain PR1-36a.

12. A biologically pure culture of *Bacillus licheniformis* strain PR1-36a.

* * * * *